(12) United States Patent
Brydon et al.

(10) Patent No.: US 6,240,921 B1
(45) Date of Patent: Jun. 5, 2001

(54) AUTOMATED STOP/START CONTROL IN THE ADMINISTRATION OF CPAP TREATMENT

(75) Inventors: John William Ernest Brydon, Wollstonecraft; Michel Calluaud, Ryde, both of (AU)

(73) Assignee: ResMed, Ltd. (AU)

(*) Notice: Subject to any disclaimer, the term of this patent is extended or adjusted under 35 U.S.C. 154(b) by 0 days.

(21) Appl. No.: 08/837,672

(22) Filed: Apr. 22, 1997

Related U.S. Application Data (62) Division of application No. 08/347,552, filed on Nov. 29, 1994.

(30) Foreign Application Priority Data

Dec. 1, 1993 (AU) ................................................. PM2725

(51) Int. Cl.[7] ............................... A62B 7/00; A62B 9/00
(52) U.S. Cl. ........................ 128/205.23; 128/205.25; 128/204.18; 128/204.21
(58) Field of Search .................. 128/202.22, 204.18, 128/204.21, 204.22, 204.23, 204.24, 205.23, 205.25

(56) References Cited

U.S. PATENT DOCUMENTS

| | | |
|---|---|---|
| Re. 35,295 | 7/1996 | Estes et al. |
| Re. 35,339 | 10/1996 | Rapoport . |
| 3,073,301 * | 1/1963 | Hay et al. ............ 128/204.26 |
| 3,099,985 | 8/1963 | Wilson et al. |
| 3,502,100 | 3/1970 | Jonson . |
| 3,595,228 | 7/1971 | Simon et al. |
| 3,726,270 | 4/1973 | Griffis et al. |
| 3,741,208 | 6/1973 | Jonsson et al. |
| 3,773,044 | 11/1973 | Wallace . |
| 3,783,893 | 1/1974 | Davison . |
| 3,834,383 | 9/1974 | Wiegl et al. |
| 3,840,006 | 10/1974 | Buck et al. |
| 3,863,630 | 2/1975 | Cavallo . |
| 3,903,875 | 9/1975 | Hughes . |
| 3,914,994 | 10/1975 | Banner . |
| 3,932,054 | 1/1976 | McKelvey . |

(List continued on next page.)

FOREIGN PATENT DOCUMENTS

| | | |
|---|---|---|
| 59270/90 | 12/1990 | (AU) . |
| 622221/90 | 3/1991 | (AU) . |
| 33877/93 | 4/1993 | (AU) . |
| 38508/93 | 7/1993 | (AU) . |
| 48748/93 | 9/1993 | (AU) . |

(List continued on next page.)

OTHER PUBLICATIONS

J Krieger et al., Eur Resp J, pp 1:436–438, "Objective Measurement of Compliance with Nasal CPAP Treatment for Obstructive Sleep Apnea Syndrome.", 1988.*

MK Reeves Hoche et al., Am Review of Resp Disease, vol. 141: p. A862 "An Objective Trial of Nasal Continuous Positive Airway Pressure Treatment Compliance.", 1990.*

R. Idatna, Am Review of Resp Disease, vol. 141: p. A863, "A Multicentric Survey of Long Term Compliance with Nasal CPAP Treatment in Patients with Obstructive Sleep Apnea Syndrome.", 1990.*

(List continued on next page.)

Primary Examiner—Glenn K. Dawson
Assistant Examiner—Joseph F. Weiss, Jr.
(74) Attorney, Agent, or Firm—Pillsbury Winthrop LLP (57) ABSTRACT

Method for automatic stop-start control of a breathing apparatus. Automatic starting and stopping of the device based upon the determination of a user wearing the mask by way of proximity sensors determining that a user is physically in contact with the mask in order to start the device and stopping the device when the proximity sensors determine the user is not in physical contact with the mask.

5 Claims, 7 Drawing Sheets

U.S. PATENT DOCUMENTS

| | | |
|---|---|---|
| 3,961,627 | 6/1976 | Ernst et al. . |
| 3,972,327 | 8/1976 | Ernst et al. . |
| 3,985,467 | 10/1976 | Lefferson . |
| 3,992,598 | 11/1976 | Welsh et al. . |
| 3,995,661 | 12/1976 | Van Fossen . |
| 4,109,749 | 8/1978 | Sweet . |
| 4,119,096 | 10/1978 | Drews . |
| 4,206,754 | 6/1980 | Cox et al. . |
| 4,239,039 | 12/1980 | Thompson . |
| 4,249,527 | 2/1981 | Ko et al. . |
| 4,301,833 | 11/1981 | Donald, III . |
| 4,312,235 | 1/1982 | Daigle . |
| 4,345,592 * | 8/1982 | Giorgini et al. ................ 128/204.26 |
| 4,345,593 * | 8/1982 | Sullivan et al. ................ 128/204.26 |
| 4,347,468 | 8/1982 | Wilke . |
| 4,387,722 | 6/1983 | Kearns . |
| 4,396,034 | 8/1983 | Cherniak . |
| 4,430,995 | 2/1984 | Hilton . |
| 4,433,685 * | 2/1984 | Giorgini et al. ................ 128/204.26 |
| 4,448,058 | 5/1984 | Jaffe et al. . |
| 4,449,525 | 5/1984 | White et al. . |
| 4,481,944 | 11/1984 | Bunnell . |
| 4,499,914 | 2/1985 | Schebler . |
| 4,519,399 | 5/1985 | Hori . |
| 4,530,334 | 7/1985 | Pagdin . |
| 4,537,190 | 8/1985 | Caillot et al. . |
| 4,558,710 | 12/1985 | Eichler . |
| 4,570,631 | 2/1986 | Durkan . |
| 4,579,114 | 4/1986 | Gray et al. . |
| 4,592,880 | 6/1986 | Murakami . |
| 4,630,614 | 12/1986 | Atlas . |
| 4,637,386 | 1/1987 | Baum . |
| 4,655,213 | 4/1987 | Rapoport et al. . |
| 4,677,975 | 7/1987 | Edgar et al. . |
| 4,686,974 | 8/1987 | Sato et al. . |
| 4,747,403 | 5/1988 | Gluck et al. . |
| 4,773,411 | 9/1988 | Downs . |
| 4,782,832 | 11/1988 | Trimble et al. . |
| 4,795,314 | 1/1989 | Prybella et al. . |
| 4,802,485 | 2/1989 | Bowers et al. . |
| 4,819,629 | 4/1989 | Jonson . |
| 4,823,788 | 4/1989 | Smith et al. . |
| 4,827,922 | 5/1989 | Champain et al. . |
| 4,838,257 | 6/1989 | Hatch . |
| 4,838,258 | 6/1989 | Dryden et al. . |
| 4,856,506 | 8/1989 | Jinotti . |
| 4,870,960 | 10/1989 | Hradek . |
| 4,870,963 | 10/1989 | Carter . |
| 4,905,687 | 3/1990 | Ponkala . |
| 4,913,401 | 4/1990 | Handke . |
| 4,915,103 | 4/1990 | Visveshwara . |
| 4,928,684 | 5/1990 | Breitenfelder et al. . |
| 4,938,210 | 7/1990 | Shene . |
| 4,938,212 | 7/1990 | Snook et al. . |
| 4,944,310 | 7/1990 | Sullivan . |
| 4,957,107 | 9/1990 | Sipin . |
| 4,986,269 | 1/1991 | Hakkinen . |
| 4,989,599 | 2/1991 | Carter . |
| 5,009,635 | 4/1991 | Scarberry . |
| 5,024,219 | 6/1991 | Dietz . |
| 5,046,491 | 9/1991 | Derrick . |
| 5,048,515 * | 9/1991 | Sanso ............... 128/204.26 |
| 5,063,922 | 11/1991 | Hakkinen . |
| 5,063,938 | 11/1991 | Beck et al. . |
| 5,065,756 | 11/1991 | Rapoport . |
| 5,099,837 | 3/1992 | Russel, Sr. et al. . |
| 5,105,354 | 4/1992 | Nishimura . |
| 5,107,830 | 4/1992 | Younes . |
| 5,107,831 | 4/1992 | Halpern et al. . |
| 5,117,819 | 6/1992 | Servidio et al. . |
| 5,129,390 | 7/1992 | Chopin et al. . |
| 5,134,995 * | 8/1992 | Gruenke et al. ................ 128/204.23 |
| 5,148,802 | 9/1992 | Sanders et al. . |
| 5,161,525 * | 11/1992 | Kimm et al. ..................... 128/204.26 |
| 5,165,398 | 11/1992 | Bird . |
| 5,178,138 | 1/1993 | Walstrom et al. . |
| 5,183,983 | 2/1993 | Knop . |
| 5,199,424 * | 4/1993 | Sullivan et al. ................ 128/204.18 |
| 5,203,343 * | 4/1993 | Axe et al. ........................... 128/725 |
| 5,230,330 | 7/1993 | Price . |
| 5,231,979 | 8/1993 | Rose et al. . |
| 5,231,983 | 8/1993 | Matson et al. . |
| 5,239,994 | 8/1993 | Atkins . |
| 5,239,995 | 8/1993 | Estes et al. . |
| 5,245,995 * | 9/1993 | Sullivan et al. ................ 128/204.23 |
| 5,259,373 * | 11/1993 | Gruenke et al. ................ 128/204.23 |
| 5,271,391 | 12/1993 | Graves . |
| 5,280,784 | 1/1994 | Kohler . |
| 5,293,864 | 3/1994 | McFadden . |
| 5,303,698 | 4/1994 | Tobia et al. . |
| 5,303,700 | 4/1994 | Weismann et al. . |
| 5,305,787 | 4/1994 | Thygesen . |
| 5,311,875 | 5/1994 | Stasz . |
| 5,313,937 | 5/1994 | Zdrojkowski . |
| 5,320,092 * | 6/1994 | Ryder ............................. 128/202.22 |
| 5,322,057 | 6/1994 | Raabe et al. . |
| 5,335,654 * | 8/1994 | Rapoport ........................ 128/204.23 |
| 5,335,656 | 8/1994 | Bowe et al. . |
| 5,343,878 | 9/1994 | Scarberry et al. . |
| 5,353,788 | 10/1994 | Miles . |
| 5,373,842 | 12/1994 | Olsson et al. . |
| 5,388,571 | 2/1995 | Roberts et al. . |
| 5,390,666 * | 2/1995 | Kimm et al. ..................... 128/204.26 |
| 5,398,673 | 3/1995 | Lambert . |
| 5,400,777 | 3/1995 | Olsson et al. . |
| 5,404,871 | 4/1995 | Goodman et al. . |
| 5,433,193 * | 7/1995 | Sanders et al. ................ 128/204.18 |
| 5,443,061 | 8/1995 | Champain et al. . |
| 5,458,137 * | 10/1995 | Axe et al. ....................... 128/204.23 |
| 5,479,920 | 1/1996 | Piper et al. . |
| 5,490,502 | 2/1996 | Rapoport et al. . |
| 5,492,113 | 2/1996 | Estes et al. . |
| 5,503,146 * | 4/1996 | Froehlich et al. ............... 128/204.23 |
| 5,509,404 | 4/1996 | Lloyd et al. . |
| 5,509,414 | 4/1996 | Hok . |
| 5,517,983 * | 5/1996 | Deighan et al. ................ 128/204.23 |
| 5,522,382 * | 6/1996 | Sullivan et al. ................ 128/204.23 |
| 5,526,805 | 6/1996 | Lutz et al. . |
| 5,535,738 | 7/1996 | Estes et al. . |
| 5,535,739 | 7/1996 | Rapoport et al. . |
| 5,537,997 | 7/1996 | Mechlenburg et al. . |
| 5,540,219 | 7/1996 | Mechlenburg et al. . |
| 5,540,220 | 7/1996 | Gropper . |
| 5,546,933 | 8/1996 | Rapoport et al. . |
| 5,549,106 * | 8/1996 | Gruenke et al. ................ 128/204.23 |
| 5,551,418 | 9/1996 | Estes et al. . |
| 5,551,419 * | 9/1996 | Froehlich et al. ............... 128/204.23 |
| 5,567,127 | 10/1996 | Wentz . |
| 5,570,682 | 11/1996 | Johnson . |
| 5,598,838 | 2/1997 | Servidio et al. . |
| 5,608,647 | 3/1997 | Rubsamen et al. . |
| 5,617,846 | 4/1997 | Graetz et al. . |
| 5,632,269 | 5/1997 | Zdrojkowski . |
| 5,633,552 | 5/1997 | Lee et al. . |
| 5,642,730 | 7/1997 | Baran . |
| 5,645,053 * | 7/1997 | Remmers et al. ............... 128/204.23 |
| 5,645,054 | 7/1997 | Cotner et al. . |
| 5,655,520 | 8/1997 | Howe et al. . |
| 5,655,522 | 8/1997 | Mechlenburg et al. . |
| 5,660,171 * | 8/1997 | Kimm et al. ..................... 128/204.23 |
| 5,666,946 | 9/1997 | Langenback . |

| | | |
|---|---|---|
| 5,682,878 | 11/1997 | Ogden . |
| 5,685,296 | 11/1997 | Zdrojkowski et al. . |
| 5,701,883 | 12/1997 | Hete et al. . |
| 5,704,345 | 1/1998 | Berthon-Jones . |
| 5,715,812 * | 2/1998 | Deighan et al. ............ 128/204.23 |
| 5,730,121 | 3/1998 | Hawkins . |
| 5,740,795 | 4/1998 | Brydon . |
| 5,794,615 | 8/1998 | Estes . |
| 5,823,187 | 10/1998 | Estes et al. . |

FOREIGN PATENT DOCUMENTS

| | | |
|---|---|---|
| 52628/93 | 7/1994 | (AU) . |
| 79174/94 | 6/1995 | (AU) . |
| 34471/95 | 2/1996 | (AU) . |
| 40711/95 | 4/1996 | (AU) . |
| 34354/95 | 5/1996 | (AU) . |
| 39130/95 | 6/1996 | (AU) . |
| 42027/97 | 2/1998 | (AU) . |
| 459104 | 4/1928 | (DE) . |
| 23 35 848 A1 | 2/1975 | (DE) . |
| 3015279 A1 | 10/1981 | (DE) . |
| 34 02 603 A1 | 8/1985 | (DE) . |
| 3537507 A1 | 4/1987 | (DE) . |
| 3539073 A1 | 5/1987 | (DE) . |
| 4432219 C1 | 4/1996 | (DE) . |
| 0 062 166 A2 | 10/1982 | (EP) . |
| 0 066 451 A1 | 12/1982 | (EP) . |
| 0 088 761 | 9/1983 | (EP) . |
| 0 164 500 A2 | 3/1985 | (EP) . |
| 0 171 321 | 2/1986 | (EP) . |
| 0 185 980 | 7/1986 | (EP) . |
| 0 236 850 A2 | 9/1987 | (EP) . |
| 0 872 643 A2 | 3/1988 | (EP) . |
| 298 367 A2 | 1/1989 | (EP) . |
| 0 388 525 A1 | 9/1990 | (EP) . |
| 0 425 092 A1 | 5/1991 | (EP) . |
| 0 481 459 A1 | 4/1992 | (EP) . |
| 481 459 A1 | 4/1992 | (EP) . |
| 0549299 A2 | 6/1993 | (EP) . |
| 606 687 A2 | 7/1994 | (EP) . |
| 0 714 670 A2 | 12/1994 | (EP) . |
| 0 656 216 A2 | 6/1995 | (EP) . |
| 0 661 071 A1 | 7/1995 | (EP) . |
| 178 925 A2 | 4/1996 | (EP) . |
| 0 709 107 A1 | 5/1996 | (EP) . |
| 0 788 805 A2 | 8/1997 | (EP) . |
| 0 839 545 A1 | 5/1998 | (EP) . |
| 2 574 657 A1 | 6/1986 | (FR) . |
| 2 672 221 A1 | 8/1992 | (FR) . |
| 2682042 A1 | 4/1993 | (FR) . |
| 1432571 | 4/1976 | (GB) . |
| 1 444 053 | 7/1976 | (GB) . |
| 2 077 444 | 12/1981 | (GB) . |
| 2 147 506 | 5/1985 | (GB) . |
| 2 164 569 | 3/1986 | (GB) . |
| 2 205 167 | 11/1988 | (GB) . |
| 0 254 700 | 10/1992 | (GB) . |
| 2 271 811 | 4/1994 | (GB) . |
| 2 294 400 | 5/1996 | (GB) . |
| 54-104369 | 8/1979 | (JP) . |
| 60-212607 | 10/1985 | (JP) . |
| 62-103297 | 4/1987 | (JP) . |
| 63-275352 | 11/1988 | (JP) . |
| 2-173397 | 12/1988 | (JP) . |
| 4-70516 | 3/1992 | (JP) . |
| 06249741 A | 9/1994 | (JP) . |
| 6-249742 | 9/1994 | (JP) . |
| 07280609 | 10/1995 | (JP) . |
| 80119610 | 1/1996 | (JP) . |
| 238077 | 11/1969 | (RU) . |
| 467041 | 5/1992 | (SE) . |
| 1710064 A1 | 2/1992 | (SU) . |
| WO 80/01044 | 5/1980 | (WO) . |
| WO 82/03326 | 10/1982 | (WO) . |
| WO 82/03548 | 10/1982 | (WO) . |
| WO 86/05965 | 10/1986 | (WO) . |
| WO 86/06969 | 12/1986 | (WO) . |
| WO 87/02577 | 5/1987 | (WO) . |
| WO 88/10108 | 12/1988 | (WO) . |
| WO 90/14121 | 11/1990 | (WO) . |
| WO 92/11054 | 7/1992 | (WO) . |
| WO 92/15353 | 9/1992 | (WO) . |
| WO 92/22244 | 12/1992 | (WO) . |
| WO 93/08857 | 5/1993 | (WO) . |
| WO 93/09834 | 5/1993 | (WO) . |
| WO 93/21982 | 11/1993 | (WO) . |
| WO 94/16759 | 8/1994 | (WO) . |
| WO 94/20051 | 9/1994 | (WO) . |
| WO 94/23780 | 10/1994 | (WO) . |
| WO 95/32016 | 11/1995 | (WO) . |
| WO 96/16688 | 6/1996 | (WO) . |
| WO 96/40337 | 12/1996 | (WO) . |
| WO 97/02064 | 1/1997 | (WO) . |
| WO 97/10019 | 3/1997 | (WO) . |
| WO 97/10868 | 3/1997 | (WO) . |
| WO 97/15343 | 5/1997 | (WO) . |
| WO 97/28838 | 8/1997 | (WO) . |
| WO 97/41812 | 11/1997 | (WO) . |
| WO 98/06449 | 2/1998 | (WO) . |
| WO 98/25662 | 6/1998 | (WO) . |
| WO 98/33433 | 8/1998 | (WO) . |
| WO 98/35715 | 8/1998 | (WO) . |
| WO 98/36245 | 8/1998 | (WO) . |
| WO 98/36338 | 8/1998 | (WO) . |
| WO 98/47554 | 10/1998 | (WO) . |
| WO 98/57691 | 12/1998 | (WO) . |

OTHER PUBLICATIONS

Kribbs et al., Brian Info Ser/Brian Research Inst, UCLA, Sleep Research vol. 20, p 270 "Objective Monitoring of Nasal CPAP Usage Patterns in OSAS Patinets.", 1991.*

Derwent: Flowmeter for fluids–has turbine transducer and volumetric sensor for simultaneous calibration.

Mark Kantrowitz, Erik Horskotte and Cliff Joslyn; "Answers to Frequently Asked Questions about Fuzzy Logic and Fuzzy Expert Systems" Version 1.24 last Modified 20 2 96.

New! Breas PV 100 CPAP First Class Quality and Function. At the right Price; Jul. 04, 1998, pp 1–2.

PV 101 Bi Level CPAP and PV 102 Bi–Level Time; pp. 1–3.

Prodigy Medical Supplies Co. Ltd.; CPAP.

Puritan Bennett; Companion 318 Nasal CPAP System; 5/93.

Nellcor Puritan Bennett; Announcing the Goodnight 314 and GoodKnight 318 Nasal CPAP Systems.

Puritan Bennett; Clean, Quiet, and Comfortable . . . The Companion's 515 Nasal CPAP System; 6/88.

DeVilbiss Night Guard Nasal CPAP for the Treatment of Obstructive Sleep Apnea.

Sunrise; DeVilbiss Horizon LT 8001 Nasal CPAP Therapy Small in Size, big on features; 8/97.

Devilbiss; Revitalizer Soft Start; The Facts Speak for Themselves, 1992.

Tranquility; Performance CPAP Advantage.

Healthdyne International; Tranquility Plus.

Respironics Inc.; Respironics' Solo CPAP System Provides Simplified OSA Therapy at an Outstanding value; Sep. 19, 1996.

Respironics Inc.; The First Family of OSA Therapy; 1991.

Fisher & Paykel Healthcare; HC200 Series Nasal CPAP Blower & Heated Humidifier.

Pierre Medical; Morphee Plus appareil de traitement des apnees du sommeil manuel d'utilisation.

Weinmann:Hamburg; Somnotron nCPAP–Great WM 2300, 11/91.

Puritan Bennett; 515a Part of Our Blueprint for the Future; 03/90.

Puritan Bennett; Companion 320 I/E Bi–Level Respiratory System; 4/93.

ResMed; Sullivan VPAP II & II ST.

ResMed; The Sullivan V Family of CPAP Systems; 1996.

ResMed; The AutoSet Portable II; 1997.

ResMed; Sullivan Nasal CPAP System.

ResMed; The Sullivan IIID; 1995.

ResMed; The Sullivan Comfort; 1996.

DeVilbiss a Division of Sunrise Medical; Expand your Horizons With The Horizons; 1995.

Healthdyne Technologies; Home Health Care Dealer; The Journal of Home Medical Equipment and Services/Supplier; Nov. and Dec. 1997.

Healthdyne International; Tranquility Quest, The Compact CPAP for Greater patient comfort.

AirStep; Medical Products . . . Stand the Test of Time.

MAP Medical Progress for Physician und Patient; The Gentle Therapy for Sleep–Related Breathing Disorders.

Taema; Ventilation CP 90.

DPAP; Breath, by breath, by breath.

Lifecare; Smallest. Quietest. Smartest.

Lifecare; Quiet CPAP System for Maximum Compliance; 1991.

Lifecare; Software Nasal Mask, Custom Nasal Masks; 1991.

Nidek Medical; Silenzio.

Weinmann; Just to Fell Well, Sensitive Sleep Apnea Therapy with Somnotron 3 and Somno–Mask System.

Respironics Inc.; Aria CPAP System; 1993.

Respironics Inc.; SleepEasy III A New Dawn in Patient Compliance.

Respironics Inc.; Muliple Choice REMstar Choice Nasal CPAP System.

MaxII nCPAP and Moritz II Bi–Level Brochure.

* cited by examiner

AUTOMATED STOP/START CONTROL IN THE ADMINISTRATION OF CPAP TREATMENT

CROSS-REFERENCE TO RELATED APPLICATION

This application is a divisional of copending application Ser. No. 08/347,552, filed Nov. 29, 1994.

BACKGROUND OF THE INVENTION

1. Field of the Invention

This invention relates to automated stop/start control in the administration of continuous positive airway pressure (CPAP) treatment.

2. Background of the Invention

The administration of CPAP is common in the treatment of obstructive sleep apnea (OSA) syndrome and upper airway resistance syndrome. The fundamental disclosure of CPAP is made in the specification of International Patent Application No. PCT/AU82/00063, published under WO 82/03548.

CPAP treatment effectively acts as a pneumatic split of a patient's upper airways by the provision of a positive air pressure of approximately 10 cm $H_2O$, although pressures in the range of approximately 5–20 cm $H_2O$ are encountered. More sophisticated forms of CPAP, such as bi-level CPAP and autosetting CPAP, are described in U.S. Pat. No. 5,245,995. Common to all forms of CPAP is a nose, mouth or face mask fitted to a patient having connection via an air delivery tube to an air flow generator.

CPAP flow generators are normally switched between a standby or stop mode to a functional mode in which pressurized air or oxygen mix is supplied to the patient by a switch located on the body of, or adjacent to, the flow generator. Alternatively, a cordless radio or infra-red remote control unit can be operated by the patient at some distance from the flow generator.

In other cases the control switch (or switches), which may be electrical or pneumatic, are located in the vicinity of the patient's mask, and control signals from them are carried back to the flow generator in parallel with the interconnecting air delivery tubing. As an alternative to a nose or mouth mask, nasal prongs (cannulae) may be inserted into the nares to effect a seal between the air delivery circuit and the patient's airway. In all cases, the patient must manually depress a control button to initiate the CPAP treatment.

In this specification the term mask is to be explicitly understood as embracing a nose mask, mouth mask, nose and mouth mask and nasal prongs. Furthermore, reference to a mask being worn indicates sealing engagement with the patient's face or with the entrance to the nares. In particular, the expression "a mask being worn" embraces the embodiment of nasal prongs being inserted into the nares.

There are a number of disadvantages in the known control implementations described above. Firstly, the patient may have to reach out of bed to press a control on the flow generator. This may be difficult to do if they are already wearing the CPAP mask with its connected tubing, or if the flow generator is some distance from the bed. Secondly, a cordless remote control can be mislaid, and its batteries will run down and must be regularly charged or replaced. In some instances, too, the remote control must be directed towards the flow generator to function, however, the flow generator may be difficult to locate in a dark room. Thirdly, controls incorporated in the mask make it heavier and therefore less comfortable to wear, perhaps leading to lack of compliance with the CPAP treatment. Also, they make cleaning and disassembly more difficult for the patient using CPAP treatment apparatus at home.

SUMMARY OF THE INVENTION

It is a preferred object of the present invention to make the control of CPAP treatment, and particularly flow generators, significantly easier for patients in the start and/or stop operations.

Therefore, the invention discloses a method for controlling apparatus for the administration of continuous positive airway pressure (CPAP) treatment, the apparatus having a controllable flow generator coupled to an air delivery circuit, in turn coupled to a mask for the supply of CPAP treatment to a patient's airways, the method comprising the steps of determining that the patient is wearing said mask and, if being worn, commencing the administration of CPAP treatment.

Preferably, the determining step comprises any one or more of the steps of detecting flow of air in said air delivery circuit, detecting a pressure change in said air delivery circuit, and detecting proximity of the patient's face with said mask.

The invention further discloses a method for controlling apparatus for the administration of continuous positive airway pressure (CPAP) treatment, the apparatus having a controllable flow generator coupled to an air delivery circuit, in turn coupled to a mask for the supply of CPAP treatment to a patient's airways, the method comprising the steps of determining whether said mask is being worn by the patient and, if not being worn, ceasing CPAP treatment.

Preferably, the determining step comprises any one or more of the steps of detecting airflow in said air delivery circuit in excess of flow due to maximum CPAP treatment pressure, detecting a pressure drop in said air delivery circuit below a minimum CPAP treatment pressure, and detecting an uncontrolled change in operation of said flow generator.

The invention yet further discloses a method for controlling apparatus for the administration of continuous positive airway pressure (CPAP) treatment, the apparatus having a controllable flow generator coupled to an air delivery circuit, in turn coupled to a mask for the supply of CPAP treatment to a patient's airways, the method comprising the steps of determining whether the patient is wearing said mask and, if being worn, commencing CPAP treatment; and if not being worn, ceasing CPAP treatment.

The invention yet further discloses apparatus for controlling the administration of continuous positive airway pressure (CPAP) treatment, said apparatus having a controllable flow generator coupled to an air delivery circuit, in turn coupled to a mask for the supply of CPAP treatment to a patient's airways, and further comprising means for determining that the patient is wearing said mask, and means for commencing the administration of CPAP treatment if the mask is being worn.

Preferably, the apparatus further comprises any one or more of detection means for detecting flow of air in said air delivery circuit, detection means for detecting a pressure change in said air delivery circuit, and detection means for detecting proximity of the patient's face with the mask. Advantageously, the detection means can include a differential or static pressure transducer. Further, the detection means can include electrical circuit means mounted from said mask, the electrical characteristics of which change with proximity of the patient's face. The changing electrical characteristics can include resistance between two electrodes, capacitance between two electrodes, or the inductance of a coil means.

The invention further discloses apparatus for controlling the administration of continuous positive airway pressure (CPAP) treatment, said apparatus having a controllable flow generator coupled to an air delivery circuit, in turn coupled to a mask for the supply of CPAP treatment to a patient's airways, and further comprising means for determining whether said mask is being worn by the patient, and means for ceasing CPAP treatment if said mask is not being worn.

Preferably, the apparatus further includes detecting means for detecting air flow in said air delivery circuit in excess of flow due to maximum CPAP treatment pressure, detection means for detecting a pressure drop in said air delivery circuit continuing for a predetermined period of time, and detection means for detecting an uncontrolled change in operation of said flow generator. The detecting means can include a differential or static air pressure transducer. Further, the detecting means can include means for measuring electrical power consumption of said flow generator, or means for measuring rotational speed of said flow generator.

BRIEF DESCRIPTION OF THE DRAWINGS

A number of embodiments of the invention will now be described with reference to the accompanying drawings, in which.

DETAILED DESCRIPTION OF PREFERRED EMBODIMENT AND BEST MODE

1. Automatic Start

Embodiments of the present invention offer an improvement in controlling a CPAP flow generator by determining that the patient is wearing the CPAP mask (including, as noted above, inserted nasal prongs) and then starting the flow generator automatically, either switching to full treatment pressure or into a pressure ramp controlled by a delay timer. This determination can be achieved in any one or more of four ways.

The first such technique is the detection of the flow of air in the breathing (air delivery) circuit caused by the patient breathing. This is achieved by measurement of a change in the pressure drop across a flow restriction located in the breathing circuit, either in the proximity of the mask or the flow generator.

Figure 1A:
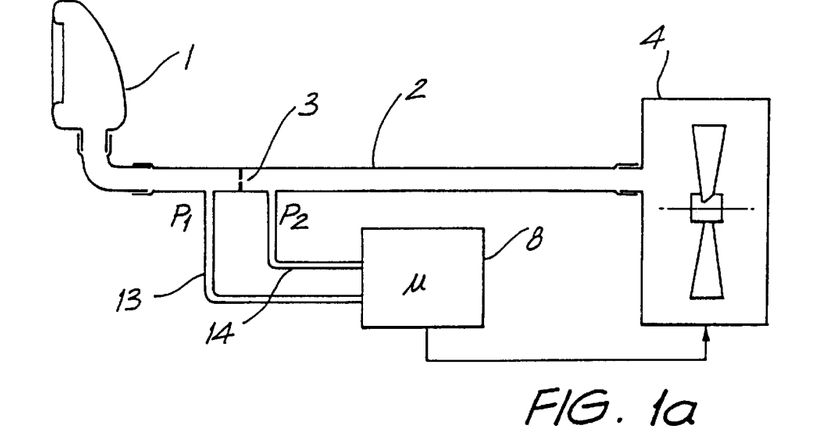
FIGS. 1a and 1b show arrangements for the determination of air flow rate as an indication of whether a CPAP mask is or is not being worn.

FIG. 1a shows a mask 1 interconnected with a flow generator (turbine) 4 by a flexible air delivery tube 2. Part-way along the delivery tube 2 is a flow restriction 3, typically in the nature of a narrowing of the diameter of the air delivery tube 2 or an iris. By measurement of the pressure drop ($P_1-P_2$) across the flow restriction 3, the presence of airflow can be detected. The pressures $P_1$, $P_2$ are supplied to the CPAP controller 8 by respective interconnecting tubes 13, 14. A pressure drop change value of X cm $H_2O$, determined by the CPAP controller 8, is set as a threshold and if exceeded is taken as indicative of airflow, and hence that the mask is being worn. Because the sense of the change in pressure drop will be opposed dependent upon inspiration or expiration, it is the modulus (or absolute value) of the pressure change compared against the threshold.

Figure 1B:
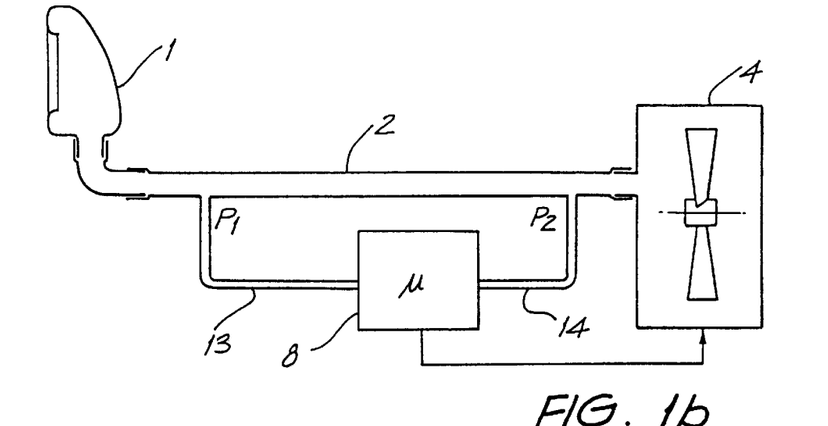

Alternatively, as shown in FIG. 1b, the measurement can be of the change in pressure drop ($P_1-P_2$) across substantially the whole length of the air delivery tube 2 itself. It is then a simple matter of comparing the modulus of the airflow rate (i.e., pressure drop having been calibrated against airflow rate) as against a threshold value (typically 200 ml/s) to determine that the mask 1 is being worn and that it is appropriate to commence the administration of CPAP treatment. The pressure $P_2$ also can be the actual flow generator delivery pressure measured at a point internally of the casing that houses the control circuits 8 and the flow generator 4.

It will be apparent that the methods described above may continually seek to commence the administration of CPAP treatment when actually being administered due to respiration causing a change in pressure drop. This, of course, presents no problem in the control of the CPAP. Furthermore, the automatic stop embodiments to be described either will override the start command, else the start command would cease being produced.

Figure 2:
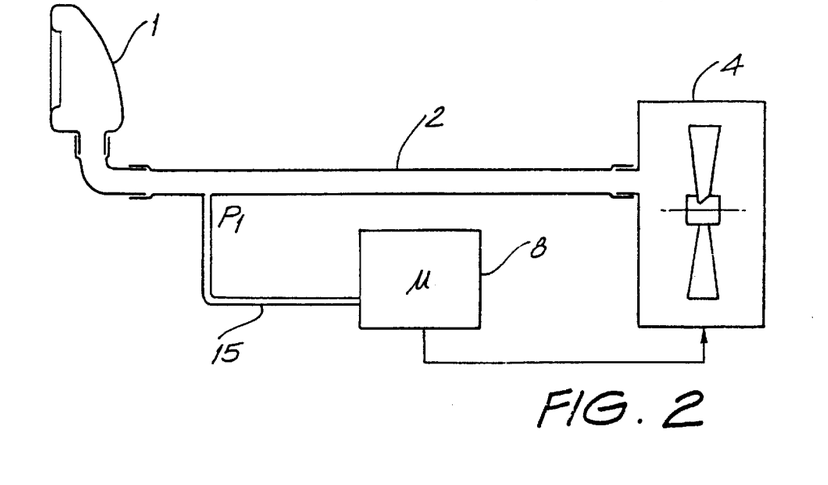
FIG. 2 shows an arrangement for the determination of a change in pressure as an indication of whether a CPAP mask is or is not being worn.

A second method of determining that the mask is being worn is by the detection of a pressure change in the breathing circuit caused by the patient breathing. As shown in FIG. 2, this is achieved by the detection of a change of the pressure $P_1$ (typically a decrease) in the air delivery tube 2 sensed by a conduit 15 connected with a pressure switch (not shown) located within the controller 8. This measurement is made in or near the mask 1, but equally could be at the flow generator 4, and its absolute value is compared against a threshold of, say, 1 cm $H_2O$ as an indication of respiration and thus the mask being worn. In the alternative, the time varying pressure signal $P_1(t)$ can be signal processed to detect the appearance of flow as a slight negative pressure, say, 1 cm $H_2O$ as the threshold indicative of inspiration, as thus indicative of the CPAP mask being worn.

A third method is the detection of the contact with, or close proximity of, the patient's face with the CPAP mask as determined via a change in the electrical characteristics of an electrical circuit having one or more electrodes located in the mask 1. The electrical characteristic can be a measure of impedance or a change in capacitive or the inductive coupling of an electrical circuit connected to the mask. Alternatively, the proximity of the patient's hand can be sensed as that person picks up the mask, as this too will affect the capacitance/inductance of the circuit.

Figure 3A:
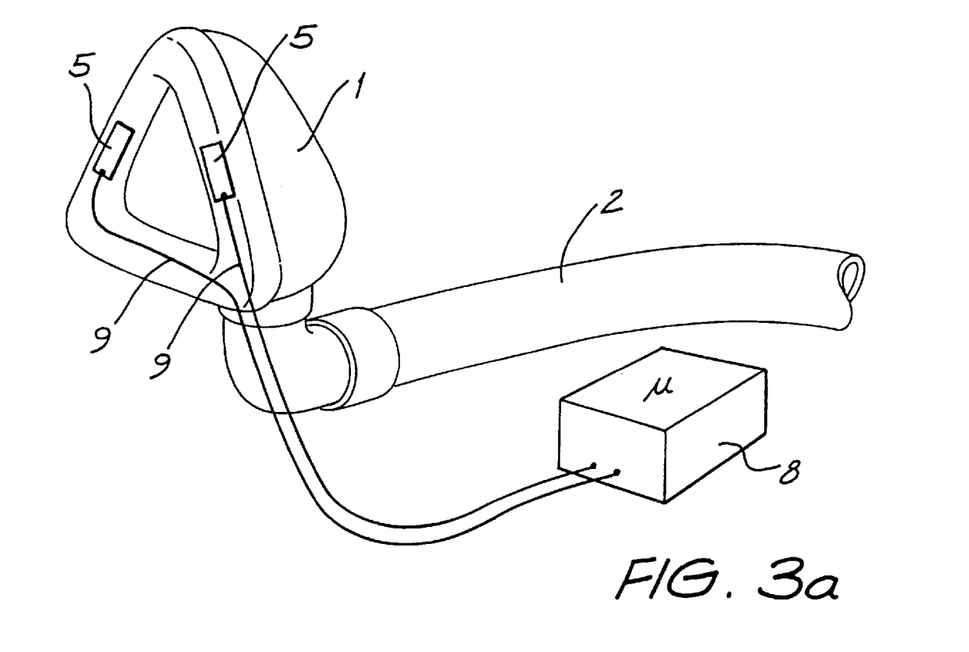
FIGS. 3a, 3b and 3c show arrangements for the determination of the proximity of a mask to a patient's face.
Figure 3B:
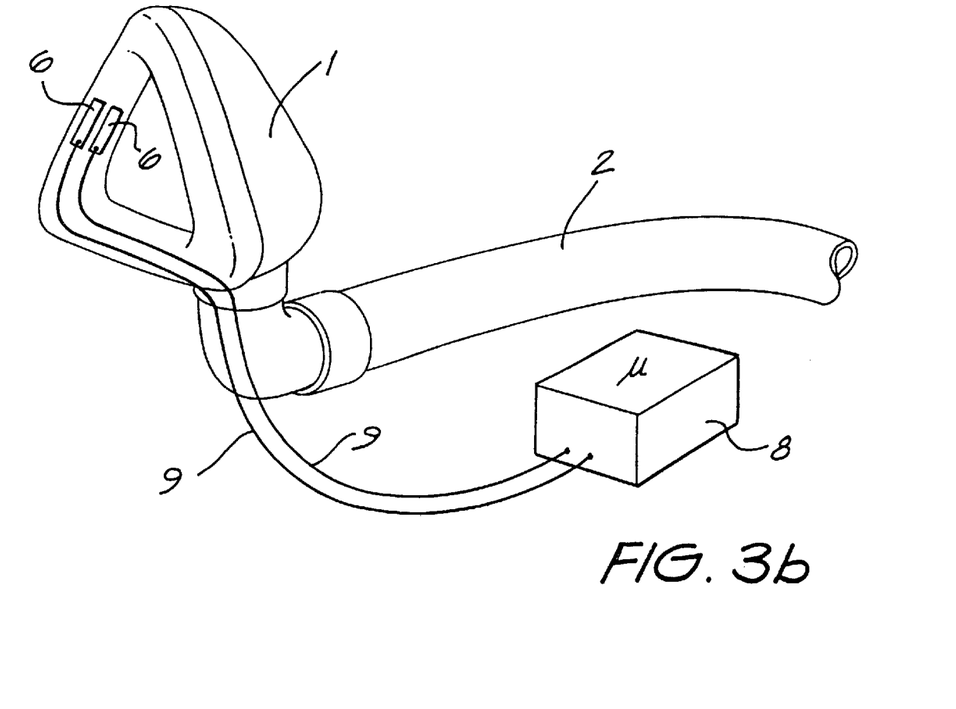
Figure 3C:
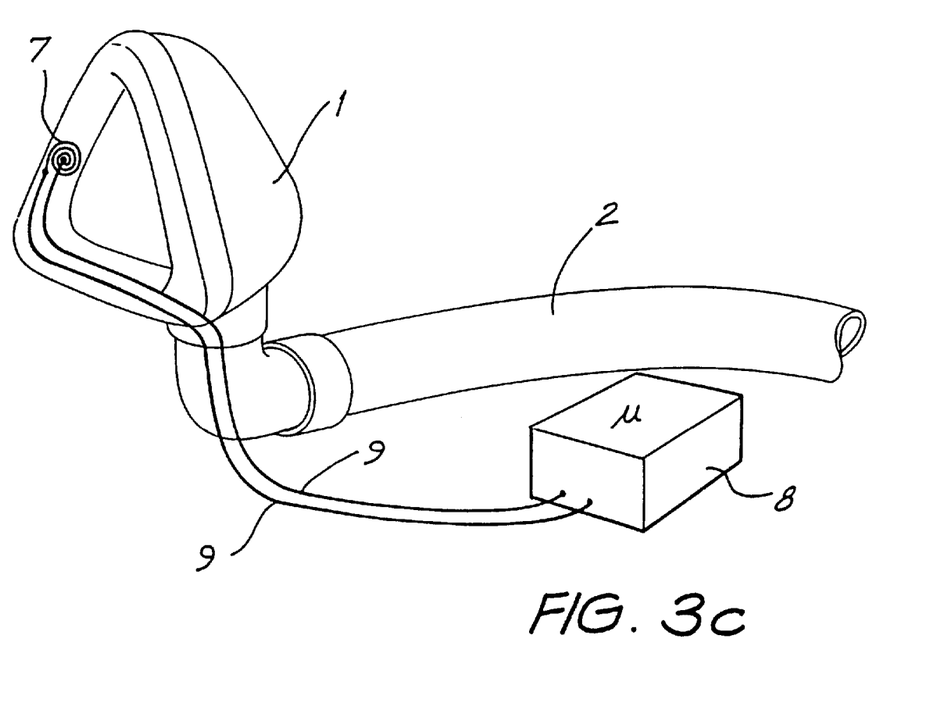

As shown in FIGS. 3a–3c, this method is achieved by the location in or near the mask 1 of two or more electrodes, shown as a pair of conductive plates 5 in FIG. 3a, capacitive plates 6 in FIG. 3b and an inductive coiled wire in FIG. 3c. Each one of these types of electrode typically is connected to the controller 8 by two interconnecting wires 9. As the mask 1 is brought in proximity to, or in contact with, the patient's face, the electrical state of the sensing circuit within the controller 8 will change. The detectable change is for the reason that a conductive (albeit high resistance) path is provided by the surface of the patient's face. The change will either be as a change in surface resistance (FIG. 3a), a change in capacitance (FIG. 3b) or a change in inductance (FIG. 3c).

Figure 4A:
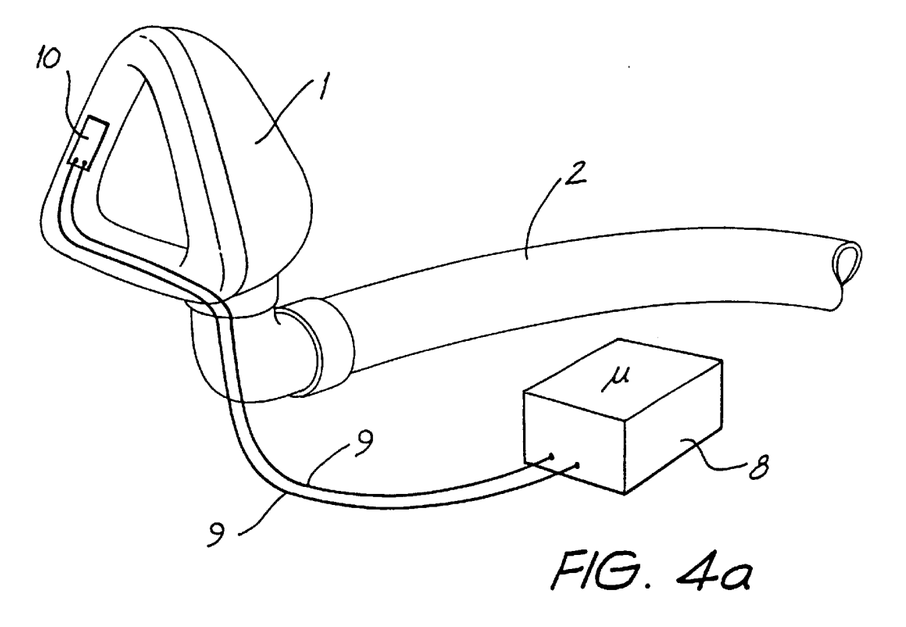
FIGS. 4a and 4b show further sensor arrangements for the determination of the proximity of a mask to a patient's face.
Figure 4B:
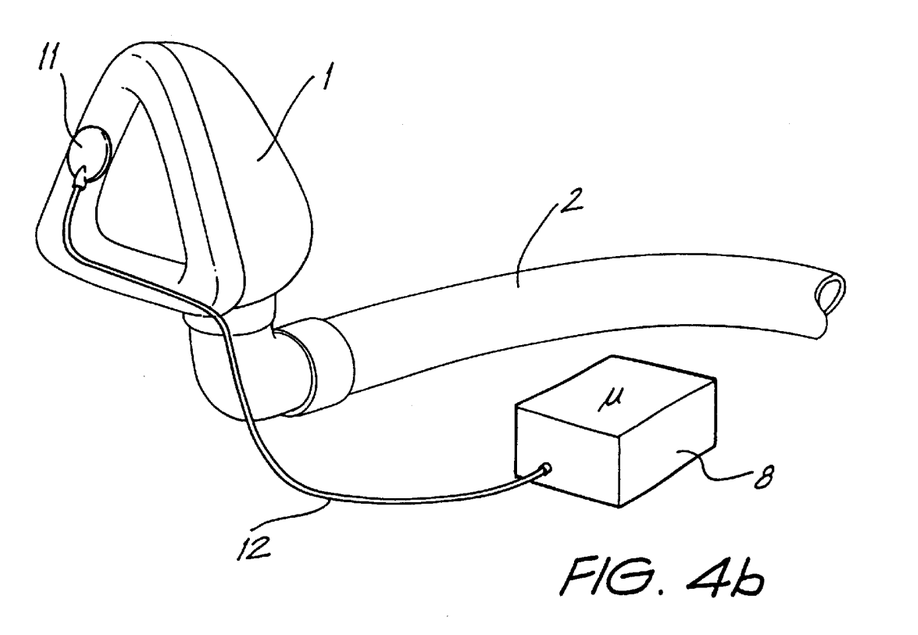

A fourth method of determining that the mask is being worn is by the detection of the contact of the mask with the patient's face, achieved via an electrical or pneumatic switch located in the mask. As shown in FIG. 4a, this is achieved by an electric switch 10 (or switches) located in the mask 1 in such a position as to be depressed or deformed when the mask 1 is brought into contact with the patient's face. The change of state of the switch 10 is therefore detectable by the controller circuitry 8, and thereafter commences the administration of CPAP treatment. Alternatively, as shown in FIG. 4b, a sac 11 of gas or liquid is similarly located on the mask 1 such that contact with the face causes distortion of the sac, and the concurrent pressure change or volumetric flow in the connecting tube 12 is detected by a pressure switch or other suitable device within the controller 8, thus again commencing the administration of CPAP treatment.

2. Automatic Stop

Embodiments of the present invention offer an improvement in controlling a CPAP flow generator by determining whether the CPAP mask is no longer being worn and then switching the flow generator 4 off automatically. This determination can be achieved in any one or more of three ways.

The first method is by the detection of increased flow of air in the breathing circuit as a result of the patient's face no longer blocking the mask air outflow. This is achieved by measurement of a change in pressure drop across a flow restriction located in the breathing circuit, either in the proximity of mask 1 or of the flow generator 4. In other words, it is essentially the same procedure as applied in the first embodiment of "automatic start," except that the change in pressure drop is of an absolute value equivalent to a different (higher) flow threshold, say 3 cm $H_2O$ continuing for three seconds or more, is used in the comparison with the measured airflow. The threshold is greater than the maximum flow due to the maximum CPAP treatment pressure. The apparatus of FIG. 1a thus applies as previously described. Alternatively, the measurement can be of the pressure drop along the length of all or part of the air delivery tubing itself, again, similarly as previously described in FIG. 1b. Accordingly, detection of an increase in airflow rate will cause the controller 8 to stop the administration of CPAP treatment. It may also be the case that an alarm is sounded in the event that the mask 1 may have inadvertently come off the patient's face, or other such occurrence.

A second method is by detecting the drop in pressure in the breathing circuit in the vicinity of the mask to a low or near-zero value, and certainly below the minimum CPAP treatment pressure, caused by the decreased restriction to flow due to the removal of the patient's face from the mask whilst CPAP treatment is being administered. This is achieved by the detection of a change of pressure, typically a decrease to less than 1 cm $H_2O$, in the breathing circuit using a pressure transducer or pressure switch. Most usually this measurement is made in the mask or near the mask in the air delivery circuit. Once again, the procedure utilizes apparatus very similar to that shown in FIG. 2. Upon sensing the decrease in pressure in excess of the threshold (again, possibly continuing for 3 seconds or more), the controller 8 will automatically stop the CPAP treatment.

A third method is by detecting an increase in the speed or the electrical supply current (power consumption) of the flow generator 4 due to the higher volumetric flow in the breathing circuit where the mask is not in place. Both instances exemplify an uncontrolled change in operation of the flow generator. Where the electric motor driving the CPAP flow generator is regulated in pressure, a sudden loss of back pressure due to a mask being removed will result in an increase in rotational speed of the turbine above the rotational speed for any treatment pressure as the turbine attempts to raise the mask pressure. For the case where the motor is speed regulated, the result of a mask being removed is a change (increase) in motor current below a set point current value in consequence of an increased flow loading on the flow generator.

Figure 5A:
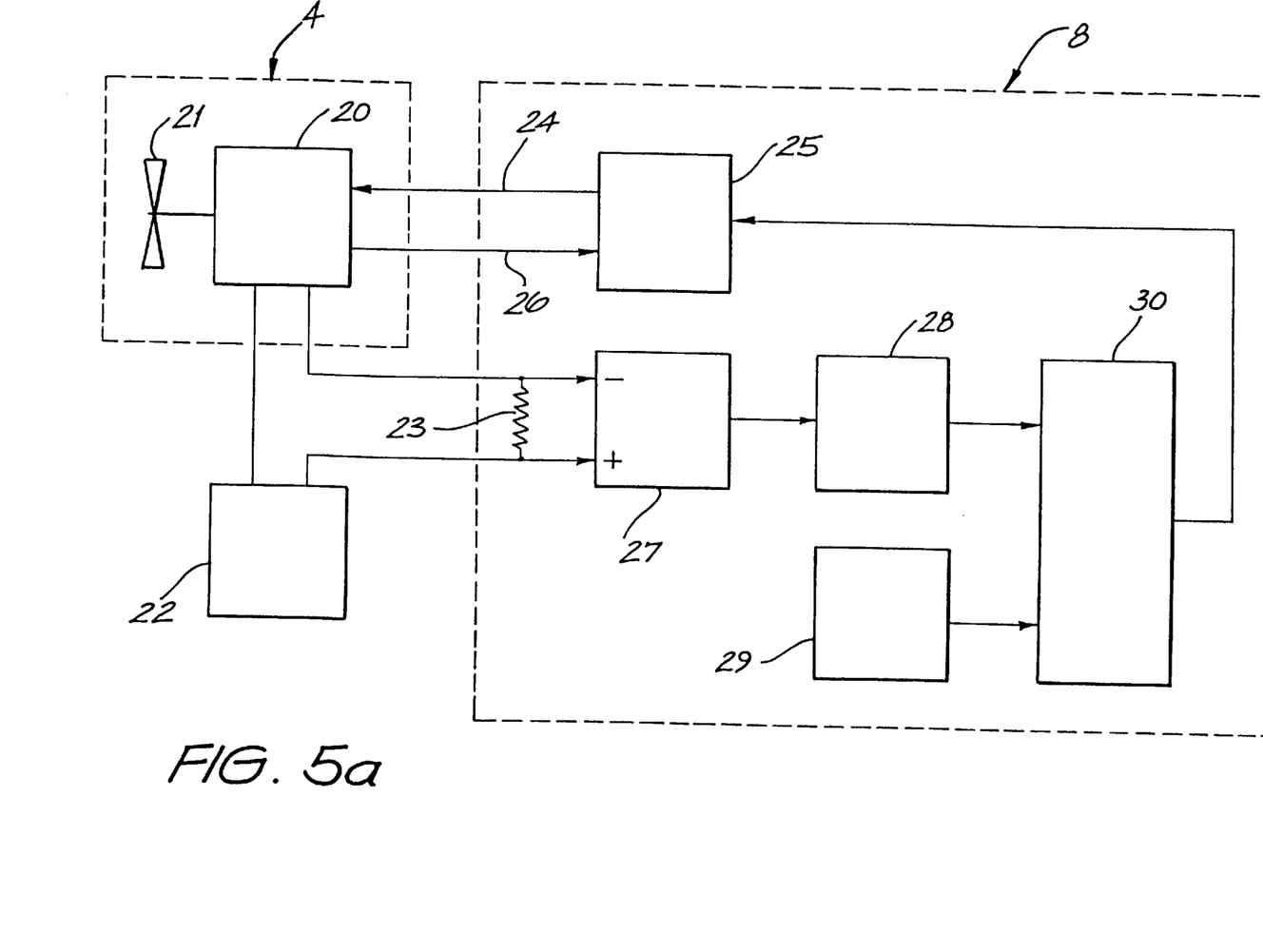
FIGS. 5a and 5b show schematic control arrangements in the determination of a CPAP mask not being worn.

FIG. 5a shows the flow generator 4 as a component motor 20 and turbine 21. The winding(s) of the motor 20 (whether AC or DC) are supplied by a power supply 22, one interconnecting cable of which includes a current sensing resistor 23. The motor 20 receives a control signal 24 supplied from a motor controller 25 that effects speed control, including stopping and starting of CPAP treatment. The motor controller 25 also receives, as a speed regulating feedback signal, an output signal 26 indicative of the motor speed.

The voltage appearing across the resistor 23 is directly proportional to current, and this voltage potential is applied to a differential amplifier 27. The output from the differential amplifier 27 passes to an averager/integrator circuit 28 that averages the pseudo-current value, and integrates it over a period of time to produce a non-linear signal now indicative of power consumption of the flow generator motor 20. A threshold generator 29 outputs a threshold value to a comparator 30 that also receives the output of the averager/integrator circuit 28. A comparison then is made between the threshold and the calculated power consumption signal, and if the threshold is exceeded, the mask 1 is determined to have been removed and the comparator 30 outputs a control signal to the motor controller 25 causing the motor 20 to be stopped, thus, in turn, stopping the administration of CPAP treatment. The threshold also may vary as a function of the selected pressure of the flow generator.

Figure 5B:
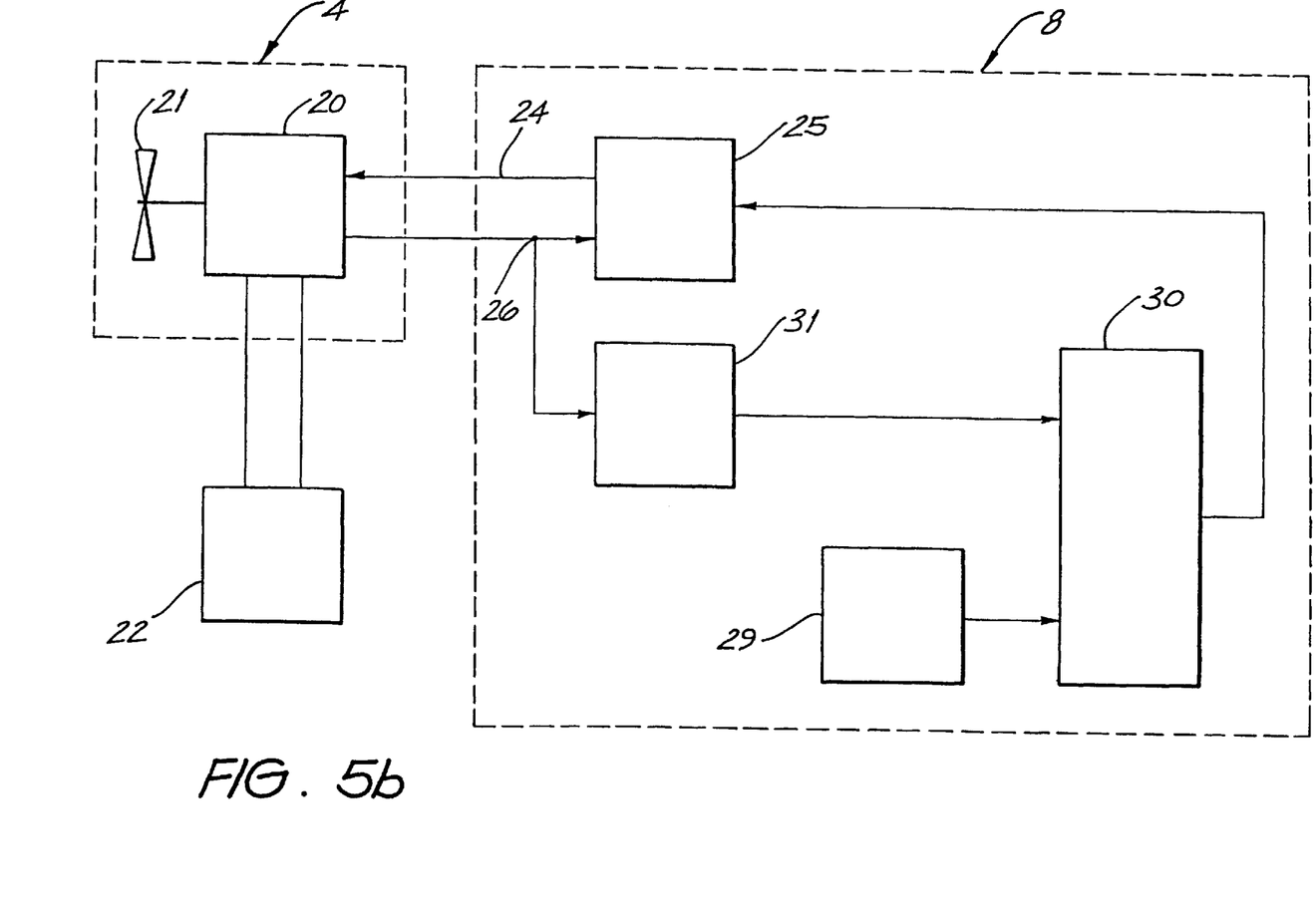

Alternatively, in flow generators where speed is not regulated, as in the case shown in FIG. 5b, the change in motor speed, typically detected from the switching signal to one winding or by the output of a Hall-effect sensor integral within the motor 20 itself, has a relation with increase in supplied pressure. FIG. 5b shows the motor speed signal 26 also being supplied to a motor speed measuring circuit 31. In a similar way as discussed above, the motor speed is compared with a threshold in the comparator 30, and if an increase in motor speed above the threshold is determined to have occurred, then a signal is passed to the motor controller 25 to cause the motor 20 to stop, hence ceasing the administration of CPAP treatment.

3. Automatic Start and Stop

Figure 6:
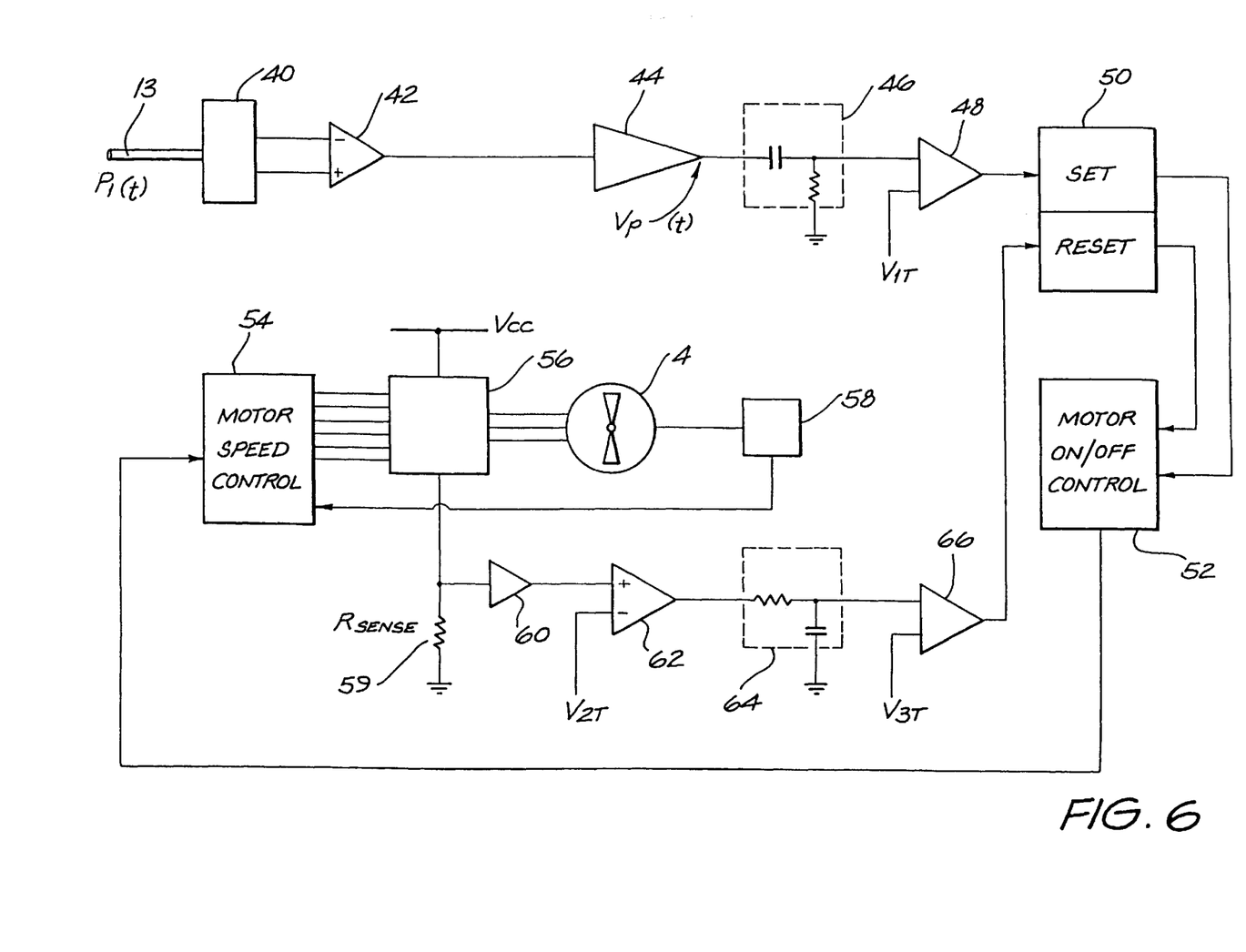
FIG. 6 shows a schematic diagram of an embodiment incorporating starting and stopping of CPAP apparatus.

FIG. 6 shows an embodiment of CPAP apparatus incorporating the features of both automatic start and automatic stop. Where convenient, like reference numerals have been used for components common with the embodiments previously described. The mask pressure signal $P_1(t)$ is provided by the tube 13 to a pressure transducer 40. The transducer 40 generates a differential output voltage proportional to the mask pressure. The differential voltages are applied to a buffering amplifier 42, and the output voltage then is filtered by a filter component 44, resulting in a voltage signal, the $V_p(t)$ proportional to the mask pressure. This voltage is AC coupled by RC circuit 46 to a comparator 48 to remove any static offset. The comparator 48 then compares the voltage signal against a threshold value $V_{1T}$.

If the mask is being worn and there is respiration, then flow occurs along the breathing circuit. This then induces a pressure within the mask, which is reflected in the voltage $V_{1T}$, and if the flow value is above some minimum (determined by the threshold $P_1(t)$) then it is determined that the mask is being worn, in which case the output of the comparator 48 goes high and causes the set output of a bistable logic circuit 50 similarly to go high and signal the motor ON/OFF control circuit 52 in turn to signal the motor speed control circuit 54 to start the flow generator 4.

The output of the motor speed controller 54 is six gating signals supplied to a double bridge inverter circuit 56. Thus the flow generator 4 is an embodiment is a fractional horse power three-winding brushless synchronous machine.

The flow generator 4 also is provided with a revolution counter, perhaps in the form of a pulse generator, that provides a rotational speed signal feedback to the motor speed controller 54.

The motor current line contains a low value resistor, $R_{sense}$, that generates a voltage, $V_{sense}$, that is directly proportional to the motor current. The voltage is passed via a low pass filter 60 to a comparator 62, where a comparison is made between the sensed voltage and a further threshold voltage, $V_{2T}$, in order to determine when there is an unexpected increase in motor current indicative of the mask no longer being worn. That is, the speed feedback mechanism will operate such that if the mask no longer is being worn, the motor speed controller 54 will control the turbine 4 such that there will be an increase in motor current due to an attempt being made to keep the mask pressure at a constant level. In the case that the motor current level exceeds that of the threshold, $V_{2T}$ then the output of the comparator 62 goes high, and is then coupled by an RC network 64, functioning as a form of timer in accordance with the time constant RxC. The output of the timer circuit 64 passes via a buffering threshold circuit 66 that discriminates the logic 0 and 1 levels to the reset input to the bistable circuit 50, in turn causing the motor ON/OFF control circuit 52 to signal the motor speed control 54 that the flow generator 4 is to be stopped.

An additional application of these principles is the detection and quantification of leaks in the breathing circuit, particularly those between the mask and the patient's face. That is, the motor power consumption or speed variation can give a confident indication, below the threshold values described, of the occurrence of mask leaks and the like. Typically, the quantities vary non-linearly with flow and are passed through linearising circuitry (or software) prior to quantification.

The combination of automatic start and stop described above can be used to provide automatic control of a CPAP flow generator, starting the machine whenever the mask is being worn, and stopping it whenever not being worn. This provides advantages for patients who get up from their beds during the night and for patients who, because of age (young or old) or physical or mental incapacity, cannot easily operate manual controls.

Numerous alterations and modifications, as would be apparent to one skilled in the art, can be made without departing from the broad scope of the present invention. All such alterations and modifications are to be considered as within the scope of the invention, embodiments of which have been hereinbefore described.

What is claimed is:

1. A method for controlling an apparatus for the administration of continuous positive airway pressure (CPAP) treatment, the apparatus having a controllable flow generator coupled to an air delivery circuit, in turn coupled to a mask for the supply of CPAP treatment to a patient's airways, the method comprising the steps of:

determining that the patient is wearing said mask, and if being worn controlling commencement of the administration of CPAP treatment by activating said flow generator, said determining steps comprising:

(a) detecting flow of air in said air delivery circuit;
   (b) detecting a pressure change in said air delivery circuit; and
   (c) detecting proximity of the patient's face with said mask.

2. A method for controlling an apparatus for the administration of continuous positive airway pressure (CPAP) treatment, the apparatus having a controllable flow generator coupled to an air delivery circuit, in turn coupled to a mask for the supply of CPAP treatment to a patient's airways, the method comprising the steps of:

determining that the patient is wearing said mask, and if being worn commencing the administration of CPAP treatment, said determining steps comprising:

(a) detecting flow of air in said air delivery circuit;
   (b) detecting a pressure change in said air delivery circuit; and
   (c) detecting proximity of the patient's face with said mask, wherein said detecting flow of air comprises the steps of detecting a change in pressure drop along at least a portion of said air delivery circuit, comparing said change in pressure drop against a threshold, and if said threshold is exceeded it is determined there is air flow.

3. A method for controlling an apparatus for the administration of continuous positive airway pressure (CPAP) treatment, the apparatus having a controllable flow generator coupled to an air delivery circuit, in turn coupled to a mask for the supply of CPAP treatment to a patient's airways, the method comprising the steps of:

determining that the patient is wearing said mask, and if being worn commencing the administration of CPAP treatment, said determining steps comprising:

(a) detecting flow of air in said air delivery circuit;
   (b) detecting a pressure change in said air delivery circuit; and
   (c) detecting proximity of the patient's face with said mask, wherein said detecting a pressure change comprises the steps of measuring mask pressure or pressure at a point along said air delivery circuit, detecting a change in said measured pressure, comparing said change in pressure against a threshold, and if said threshold is exceeded it is determined that the mask is being worn.

4. A method for controlling an apparatus for the administration of continuous positive airway pressure (CPAP) treatment, the apparatus having a controllable flow generator coupled to an air delivery circuit, in turn coupled to a mask for the supply of CPAP treatment to a patient's airways, the method comprising the steps of:

determining that the patient is wearing said mask, and if being worn commencing the administration of CPAP treatment, said determining steps comprising:

(a) detecting flow of air in said air delivery circuit;
   (b) detecting a pressure change in said air delivery circuit; and
   (c) detecting proximity of the patient's face with said mask, to the wherein said detecting proximity of said mask to the patient's face comprises the step of detecting a change in electrical characteristics of circuit means mounted from said mask.

5. The method as claimed in claim 4, wherein said characteristics of said circuit means include the resistance between two electrodes, the capacitance between two electrodes, or the inductance of a coil means.

* * * * *